United States Patent [19]

Hooper

[11] 4,031,753
[45] June 28, 1977

[54] TOTAL WATER CONTENT INSTRUMENT

[75] Inventor: Richard G. Hooper, La Crescenta, Calif.

[73] Assignee: The United States of America as represented by the Secretary of the Air Force, Washington, D.C.

[22] Filed: Aug. 20, 1976

[21] Appl. No.: 716,304

[52] U.S. Cl. .................................. 73/170 R; 73/424
[51] Int. Cl.$^2$ .......................................... G01N 1/00
[58] Field of Search ............. 73/170 R, 424, 421 R

[56] References Cited
UNITED STATES PATENTS 2,492,768  12/1949  Schaefer .......................... 73/170 R Primary Examiner—Jerry W. Myracle
Attorney, Agent, or Firm—Joseph E. Rusz; Arsen Tashjian

[57] ABSTRACT

An instrument for sampling both solid and liquid water particles in the atmosphere and continuously producing an electrical output response directly equivalent to the total percentage water content of the atmosphere sampled. The solid and/or liquid water particles are collected by using a large funnel shaped scoop of 100 cm$^2$ to allow high volume collection at nominal aircraft speeds. The water is routed into the detection device which includes a concentric cylinder flow-through capacitor that varies in capacitance according to the dielectric of the fluid enclosed.

4 Claims, 1 Drawing Figure

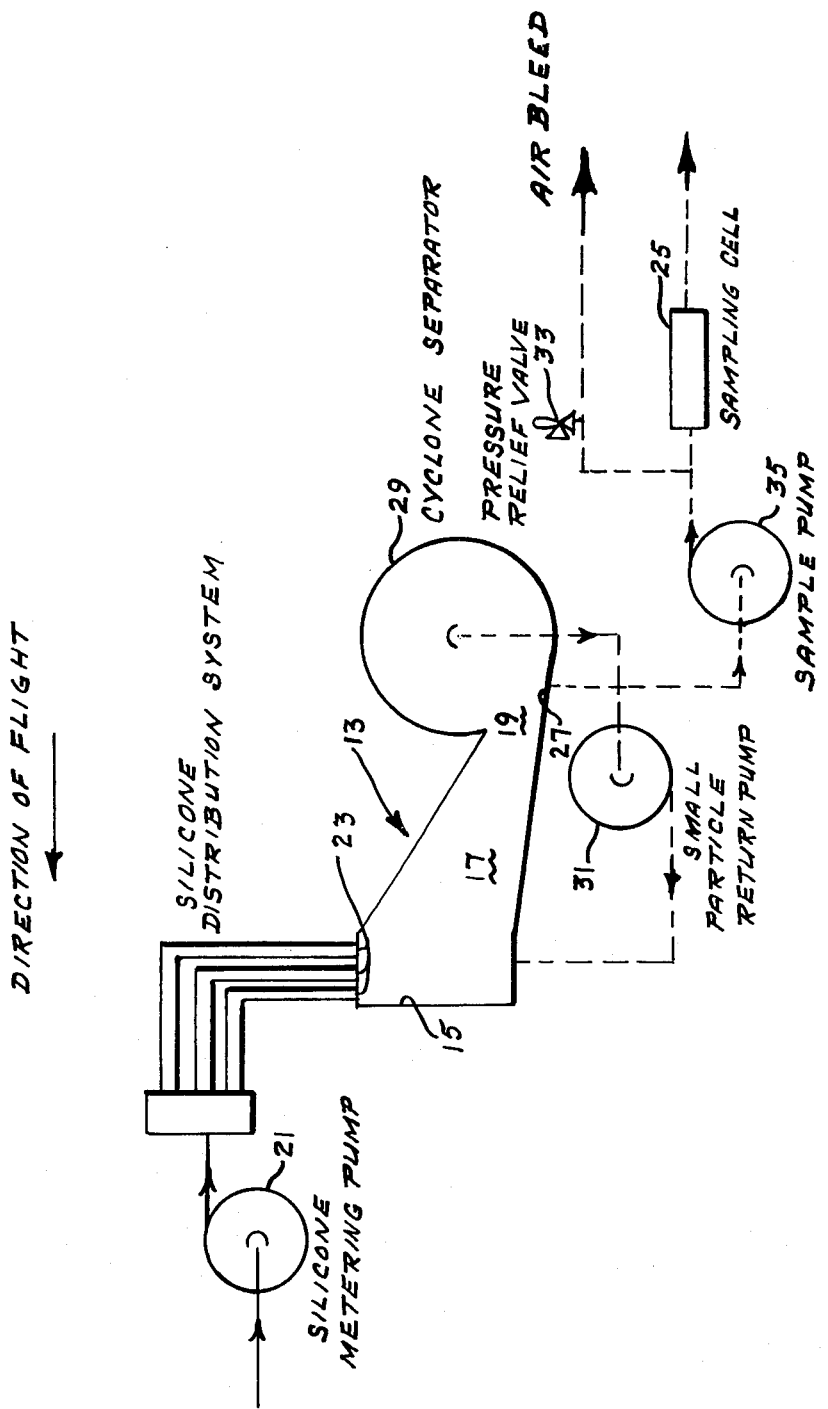

TOTAL WATER CONTENT INSTRUMENT

STATEMENT OF GOVERNMENT INTEREST

The invention described herein may be manufactured and used by or for the Government for governmental purposes without the payment of any royalty thereon.

BACKGROUND OF THE INVENTION

The invention relates to an instrument for real-time monitoring the total water content in the atmosphere and, more particularly, the instrument is concerned with sampling solid and/or liquid water particles in the atmosphere and continuously giving an electrical output response directly equivalent to the total percentage water content of the atmosphere sampled.

Meteorological instruments are available to obtain quantitative information about the weather. One particularly useful measurement concerning the state of the atmosphere is the content and quantity of liquid and solid particles of water in the upper air. A helpful instrument to make this determination would be capable of real-time monitoring of the total water content in the atmosphere. The hereinafter presented disclosure described an instrument which effectively overcomes the disadvantages of most presently known systems for measuring water content in the atmosphere and provides an instrument having the engineering parameters required to produce the desired results.

SUMMARY OF THE INVENTION

The present invention is concerned with providing a total water content instrument suitable for continuously giving an electrical output response that is directly proportional to the total percentage water content of a sample solid or liquid water particles in a sample area of the atmosphere. The sample areas can be associated with clouds of either liquid water, ice, or snow as well as areas of precipitation not necessarily defined by clouds. A large funnel shaped scoop with the wide end facing forward allows high volume collection of particles at nominal aircraft speeds. The time lag for routing of water into the detection device is around 12 seconds. The detection device is a concentric flow-through capacitor which varies in capacitance according to the dielectric of the fluid enclosed.

Accordingly, it is an object of the invention to provide an instrument capable of real-time monitoring of total water content in the atmosphere.

Another object of the invention is to provide a total water content instrument for obtaining a continuous electrical output response directly equivalent to the total percentage water content of the atmosphere sampled.

Still another object of the invention is to provide a total water content instrument which is capable of sampling clouds of either ice or liquid water, snow or areas of precipitation not necessarily defined by clouds.

A further object of the invention is to provide an instrument for monitoring the total water content in the atmosphere which includes a large funnel shaped scoop for collecting solid or liquid water particles at nominal aircraft speeds.

A still further object of the invention is to provide a total water content instrument which includes a detection device having a concentric cylinder flow-through capacitor which varies in capacitance according to the dielectric of the fluid enclosed.

Another still further object of the invention is to provide an instrument for monitoring the total water content in the atmosphere wherein silicone fluid is injected into the air stream by nozzles located around the upper perimeter of the intake opening.

These and other objects, features and advantages will become more apparent after considering the following description taken in conjunction with the annexed drawing and appended claims.

BRIEF DESCRIPTION OF THE DRAWING

The FIGURE is a schematic drawing of the flow pattern of the total water content instrument according to the invention showing the silicone distribution system at the mouth of the inlet scoop and the cyclone separator which separates and removes the smaller water particles which are returned to the inlet scoop for recycling.

DESCRIPTION OF A PREFERRED EMBODIMENT

Referring now to the drawing, the total water content instrument includes an air sampling scoop 13 having a fixed opening aperture 15 followed by a narrowing area 17 leading into a throat 19 which is positioned lower than the aperture 15.

Silicone fluid is pumped into the air stream by the silicone pump 21 through the injection nozzles 23 located around the upper perimeter of the intake opening 15. This silicone fluid flows down the back of the scoop 13 and then into the throat 19. Incoming water particles impact on the inside of the scoop 13 and become captured by the silicone fluid. The inside back of the scoop 13 is maintained at 10 degrees C by electric heating so that any ice or snow intercepted is converted to water. This facilitates transport of the water by the silicone fluid from the throat 19 to the sampling capacitor 25.

Complete separation of the water from the sampled air stream is a two step process. The first step is accomplished by impaction upon the inside of the scoop 13. Water particles which are swept past the suction port 27 at the throat 19, are pulled into the cyclone separator 29 where they are spun out. In the second step, smaller water particles removed in the cyclone separator 29 are drawn into the small particle return pump 31 and returned to the inlet 15 where they enter the scoop 13 and are picked up by the suction port 27 in the throat 19. Together, this two-step process results in a 99 percent separation of water from the air. The small volume of air remaining in the fluid stream is eliminated by a pressure relief valve 33 prior to detection by the sampling cell 25.

The collected fluid is pumped through the sampling or detection cell 25 by a gear pump 35. The parameter defining the water content of the fluid passing through the detection cell 25 operating as a capacitor is frequency, a function of the dielectric constant of the water/silicone fluid ratio. As the ratio of water to silicone fluid fluctuates, the detector circuit frequency varies in a linear relation thereto.

The water content values are calculated in the following manner:

If the ratio of water to silicone fluid plus water is designated R, then $$W = \frac{R}{1-R} O \qquad \text{Eq. 1}$$

where
O = percentage of silicone fluid by volume
W = percentage of water by volume
The relationship of R to frequency of the sensing capacitor then becomes:

$$R = MF + B \qquad \text{Eq. 2}$$

Where
F = sensing capacitor frequency
B = some external reference cell frequency
M = some proportionality factor determined empirically Consequently only the frequency of the detector circuit need be monitored in order to determine the unknown water percentage R using the empirical relationship of equation 2. Substituting the flow rate of silicone fluid for O yields flow rate of water W. Substituting this value or R into the theoretical function of equation 1 yields rate of flow of water, silicone fluid flow being held constant at a known value. Knowing the true aircraft speed and the opening area of the sampling scoop, the volumetric percentage concentration of water in air can then be calculated.

Some of the particularly unique features of the hereinbefore described total water content instrument include the use of silicone fluid with emulsifying agent and the detection method. The silicone fluid serves several functions. It encapsulates the water to prevent evaporation and assists in conducting heat from the walls of the air sampling scoop to any solid water that is sampled. It facilitates movement of the water from the throat of the collector to the sampling capacitor and is compounded with an emulsifying agent so as to flow through the capacitor smoothly. Lack of the emulsifying agent would result in erratic and unreliable output from the sensor capacitor. Owing to the extremely low dielectric constant of the silicone fluid, the capacitance of the detection cell is almost completely determined by the water fraction between the electrodes of the cell. The application of concentric cylinders to this measurement is rendered practicable by the use of the silicone fluid. The use of the concentric electrode capacitor is employed to give a frequency output proportional to the rate at which water is ingested. It does not matter how much water-silicone mixture is voided and how much is sampled once the mixture ratio has been established.

Although the invention has been illustrated in the accompanying drawing and described in the foregoing specification in terms of a preferred embodiment thereof, the invention is not limited to this embodiment or to the particular configuration shown and described. It will be apparent to those skilled in the art that certain changes, modifications and substitutions can be made, particularly with respect to the positioning of the various pumps without departing from the true spirit and scope of the appended claims.

Having thus set forth the nature of my invention, what I claim and desire to secure by Letters Patent of the United States is:

1. An instrument for sampling both solid and liquid water particles in the atmosphere and continuously producing an electrical signal directly equivalent to the total percentage water content of the atmosphere sampled, said instrument comprising an air sampling scoop of substantially funnel shaped configuration, a fixed intake aperture at the forward end of said air scoop, a narrowing area downstream said intake aperture, a throat area downstream said narrowing area, a suction port located in the throat area, a sample pump in operative communication with said suction port for drawing the water particles from the atmosphere sample therefrom, a sampling capacitor in operative communication with said sample pump for receiving the output therefrom and producing an electrical signal proportional to the water content of the atmosphere sample, and means at the throat of said air scoop for spinning out water particles which are swept past said suction port and returning the spun out water particles to the intake aperture of said air scoop.

2. The instrument for sampling both solid and liquid water particles in the atmosphere defined in claim 1 wherein the means for spinning out the water particles which are swept past the suction port include a cyclone separator having an intake operatively connected to the throat of the air scoop, and a small particle return pump connected to the output of said cyclone separator for causing the spun out water particles from the cyclone separator to be transported to the air scoop intake opening.

3. The instrument for sampling both solid and liquid water particles in the atmosphere defined in claim 2 wherein a silicone pump is operatively connected to said air scoop, and a series of injection nozzles positioned around the upper perimeter of the intake opening of said air scoop to inject silicone fluid from said silicone pump into the intake opening thereby causing the silicone fluid to flow down the back of the air scoop and into the throat such that incoming water particles that impact on the inside of the air scoop are captured by the silicone fluid.

4. The instrument for sampling both solid and liquid water particles in the atmosphere defined in claim 3 wherein a pressure relief valve is operatively connected between the output of the sampling pump and the input of the sampling capacitor thereby eliminating any small volume of air remaining in the fluid stream.

* * * * *